United States Patent
Aita et al.

(10) Patent No.: US 9,931,063 B2
(45) Date of Patent: Apr. 3, 2018

(54) SENSOR FOR MEASURING MOTOR FUNCTION, A PLASTIC BAND, AND A DEVICE FOR MEASURING MOTOR FUNCTION

(75) Inventors: Toshihiro Aita, Tokyo (JP); Akitoshi Doi, Tokyo (JP); Atsushi Ninomiya, Tokyo (JP); Mitsuru Onuma, Tokyo (JP); Akihiko Kandori, Tokyo (JP); Yuko Sano, Tokyo (JP); Norihiko Adachi, Tokyo (JP)

(73) Assignee: Hitachi Maxell, Ltd., Osaka (JP)

( * ) Notice: Subject to any disclaimer, the term of this patent is extended or adjusted under 35 U.S.C. 154(b) by 964 days.

(21) Appl. No.: 13/005,695

(22) Filed: Jan. 13, 2011

(65) Prior Publication Data

US 2011/0230789 A1 Sep. 22, 2011

(30) Foreign Application Priority Data

Mar. 17, 2010 (JP) ................................. 2010-060716

(51) Int. Cl.
*A61B 5/11* (2006.01)
*A61B 5/00* (2006.01)

(52) U.S. Cl.
CPC ............. *A61B 5/1125* (2013.01); *A61B 5/411* (2013.01); *A61B 2560/0437* (2013.01); *A61B 2562/0223* (2013.01)

(58) Field of Classification Search
CPC .......... A61B 2562/0223; A61B 5/6826; A61B 5/1125

(Continued)

(56) References Cited

U.S. PATENT DOCUMENTS 1,610,089 A * 12/1926 Heitler .................. A61F 15/006
  602/42
5,170,786 A * 12/1992 Thomas ............. A61B 5/02427
  600/310

(Continued)

FOREIGN PATENT DOCUMENTS

JP 2002159473 6/2002
JP 2005-95197 4/2005

(Continued)

OTHER PUBLICATIONS

Japanese Office Action dated Aug. 6, 2013 in corresponding Japanese Patent Application No. 2010-060716.

*Primary Examiner* — Rene Towa
*Assistant Examiner* — Huong Q. Nguyen
(74) *Attorney, Agent, or Firm* — Brundidge & Stanger, P.C.

(57) ABSTRACT

This invention provides a sensor or its related art to be easily used for measuring motor function of living body. This invention relates to a sensor for measuring motor function, which includes a magnetic field generator attached to one of two predetermined positions in a living body changing mutual distance caused by an action of the living body to have a coil board generating a magnetic field by electrification, and a magnetic field detector attached to the other of the two predetermined positions in the living body to detect the magnetic field generated by the magnetic field generator and have the coil board generating an electric current having a magnitude corresponding to a strength of the magnetic field as detected. Furthermore, each of the magnetic field generator and the magnetic field detector is provided with plastics covering a whole coil board thereof.

15 Claims, 8 Drawing Sheets

(58) Field of Classification Search
USPC .................................................. 600/344, 595
See application file for complete search history.

(56) References Cited

U.S. PATENT DOCUMENTS

| | | | | |
|---|---|---|---|---|
| 5,991,648 | A | * 11/1999 | Levin | .................... A61B 5/6829 |
| | | | | 600/344 |
| 7,419,473 | B2 | 9/2008 | Kandori et al. | |
| 2001/0053306 | A1 | * 12/2001 | Schneider | ............ B43K 23/012 |
| | | | | 401/8 |
| 2006/0084855 | A1 | * 4/2006 | Teschner et al. | .............. 600/390 |
| 2006/0244744 | A1 | 11/2006 | Kandori et al. | |
| 2007/0038067 | A1 | 2/2007 | Kandori et al. | |
| 2007/0272599 | A1 | 11/2007 | Miyashita et al. | |
| 2008/0116360 | A1 | 5/2008 | Nakayama | |
| 2008/0238414 | A1 | 10/2008 | Miyashita et al. | |
| 2008/0249406 | A1 | * 10/2008 | Naruse | ........................... 600/437 |
| 2009/0069663 | A1 | 3/2009 | Kandori et al. | |
| 2010/0099962 | A1 | * 4/2010 | Chung et al. | ................. 600/323 |

FOREIGN PATENT DOCUMENTS

| | | |
|---|---|---|
| JP | 2006-296618 | 11/2006 |
| JP | 2007-29401 | 2/2007 |
| JP | 2007-54597 | 3/2007 |
| JP | 2007-301003 | 11/2007 |
| JP | 2008129719 | 6/2008 |
| JP | 2008-246126 | 10/2008 |
| JP | 2008238414 | 10/2008 |

* cited by examiner

SENSOR FOR MEASURING MOTOR FUNCTION, A PLASTIC BAND, AND A DEVICE FOR MEASURING MOTOR FUNCTION

FIELD OF THE INVENTION

The present invention relates to a sensor for measuring motor function concerning living body (for example, human body), a plastic band for attaching the sensor to the living body, and a device for measuring motor function receiving a signal from the sensor.

BACKGROUND OF THE INVENTION

A patient suffering from Parkinson's disease or cerebral infraction is likely to happen a physical dysfunction.

Then, it has been long desired that the motor function of the patient can be exactly understood or recognized. Conventionally, a doctor has judged based on an experience, for example, by seeing that a patient practices an opening or closing action between his or her thumb and other finger, in case that the doctor judges the patient to be a good motor function or not. Then, the doctor used to judge a health condition of patient based on the experience by seeing his or her action. However, the motor function cannot be exactly judged based on such a subjective judgment.

Therefore, this applicant provides an art for measuring motor function of a subject for experiment at high accuracy by that the subject for experiment practices the opening or closing action of their fingers with coils wearing in each of the thumb and forefinger of the subject for experiment such as the patients, such that it is turned on electricity in one coil to generate a magnetic field and velocity, acceleration, or the like caused by the opening or closing action of fingers are analyzed according to a magnitude of induced electric current generated in the other coil. (Japanese patent unexamined laid-open publication No. 246,126 of 2008 will be referred to)

SUMMARY OF INVENTION

However, in the art disclosed in the above publication, it is not satisfied with factors such as a feeling of wearing or costs when the sensor is attached to fingers of subject for experiment, or conveniences (user-friendliness) when the sensor is stored in a device connecting thereto.

Accordingly, an object of the present invention is to be made in view of the above problem and to provide a sensor and its related art to be easily used for measuring motor function of a living body.

To solve the above problem, the present invention is characterized by a sensor for measuring motor function including a magnetic field generator attached to one of two predetermined positions in a living body changing mutual distance caused by an action of the living body to have a coil board generating a magnetic field by electrification, and a magnetic field detector attached to the other of the two predetermined positions in the living body to detect the magnetic field generated by the magnetic field generator and have the coil board generating an electric current having a magnitude corresponding to a strength of the magnetic field as detected. Furthermore, this sensor is characterized in that each of the magnetic field generator and the magnetic field detector is provided with plastics covering a whole coil board. The other matters will be later described. According to the present invention, a sensor or the related art to be easily used for measuring motor function in a living body can be provided.

DETAILED DESCRIPTION OF THE PREFERRED EMBODIMENT

A mode for carrying out this invention (hereinafter, referred to as "embodiment") will be described with reference to the above drawings. Although a subject for experiment means a living body (human, animal, etc.) as a subject for measuring motor function, it means human in this description. A system S for measuring motor function relating to this embodiment is indicated to make a finger-tapping movement to open or close human thumb and forefinger as soon as possible to a subject for experiment and measure the motor function of the subject for experiment in accordance with this movement of fingers.

Figure 1:
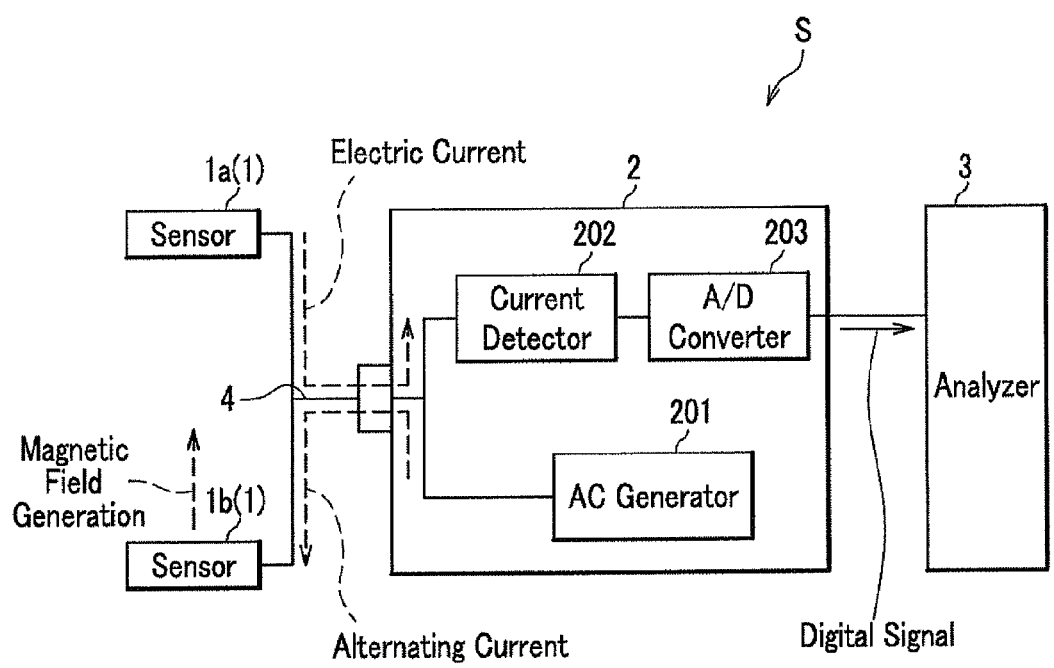
FIG. 1 is a block diagram of a sensor, a device for measuring motor function, and an analyzer relating to this embodiment.

As shown in FIG. 1, a system for measuring motor function S is constituted by a sensor 1a (magnetic field detector), 1b (magnetic field generator) (it is, hereinafter, referred to as "sensor 1" except that a distinction between the sensors 1a, 1b exists), a device for measuring motor function 2, and an analyzer 3. As a sensor for measuring motor function is constituted by the magnetic field detector and the magnetic field generator, the magnetic field detector is called by the sensor 1a, and the magnetic field generator is called by the sensor 1b, for convenience of explanation, in this embodiment. The sensor 1a, 1b are worn in two fingers (for example, thumb and forefinger) of subject for experiment. The sensor 1 is connected to a cable 4, and the cable 4 is connected to a connector 5. A constitution of the sensor 1 will be later described.

The device for measuring motor function 2 is a device positioned between the sensor 1 and the analyzer 3. This device 2 is provided with an AC generator 201, a current detector 202, and A (analog)/D (Digital) converter 203 to be materialized by various kinds of electronic circuits.

The AC generator 201 is designed to generate alternative current with predetermined cycle.

The current detector 202 is designed to detect electric current from the sensor 1 received through the cable 4 and the connector 5.

The A/D converter 203 is designed to convert a value of electric current detected by the current detector 202 to a digital signal, and output the digital signal to the analyzer 3. A constitution of the device for measuring motor function 2 will be later described.

An outline of actions of the sensor 1, the device for measuring motor function 2, and the analyzer 3 will be hereinafter described. The subject for experiment is supposed to wear the sensor 1a, 1b in two fingers to make the finger-tapping movement.

At first, the AC generator 201 of the device for measuring motor function 2 generates alternative current having a specific frequency (for example, 20 kHz etc.). The alternative current is supplied through the connector 5 and the cable 4 to the sensor 1b. The sensor 1b receiving alternative current generates a magnetic field and the magnetic field changes constantly. The sensor 1a generates an induced current by an electromagnetic induction caused by a change of magnetic field. In addition, a magnitude of the induced current becomes smaller, as a distance between the sensors 1a, 1b becomes larger.

The current detector 202 is designed to detect an induced current generated by the sensor 1a through the cable 4 and the connector 5 to supply the data to the A/D converter 203. The A/D converter 203 converts a waveform data of the data (analogue signals of the induced current) received from the current detector 202 to a waveform data of the digital signal at the predetermined sampling frequency to send the converted digital signal to the analyzer 3. The analyzer 3 is a computer device and analyzes motor function of a subject for experiment in accordance with the basis of digital signal received from the A/D converter 203.

The device for measuring motor function 2 may be appropriately provided with an amplifier circuit, a phase adjustment circuit, LPF (Low-Pass Filter), and the like, besides the above constitution. An explanation about the circuits and the like will be omitted with reference to the above publication as described in detail.

Figure 2A:
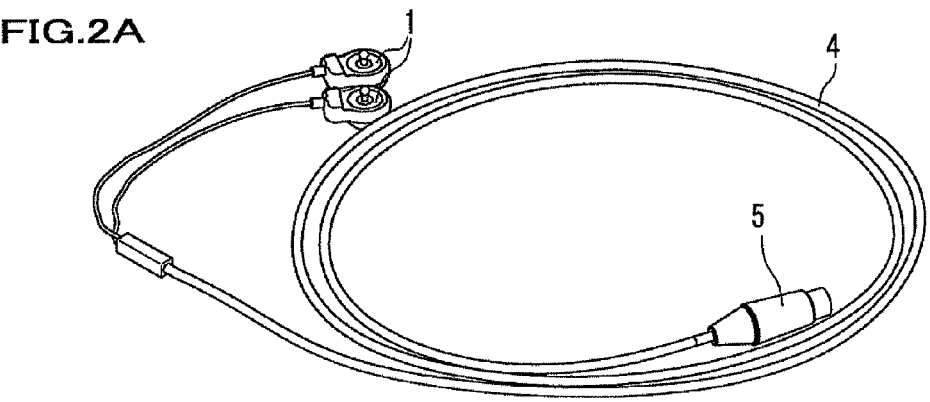
FIG. 2A is a view showing an outer configuration of sensors, cables, and connectors relating to this embodiment.

Next, the sensor 1 and a constitution of the plastic band for attaching the sensor 1 to fingers of a subject for experiment will be described. As shown in FIG. 2A, the sensor 1 is connected to the cable 4, and the cable 4 is connected to the connector 5.

Figure 2B:
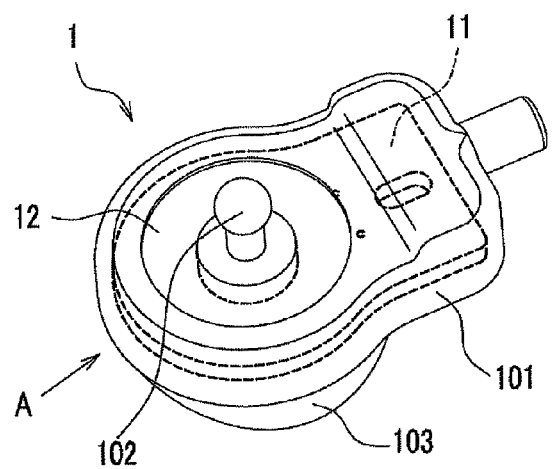
FIG. 2B is a view showing a constitution of the sensor.
Figure 2C:
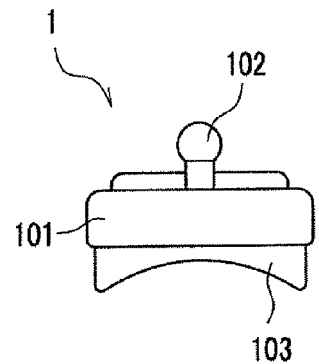
FIG. 2C is a view as the sensor seen from a direction A of FIG. 2B.

As shown in FIG. 2B, the sensor 1 is constituted by covering a coil board 11 having a coil portion 12 by a plastics 101 including a pin 102 and a nail contact portion 103. The sensor 1 can make high in strength by covering the whole coil board 11 by the plastics 101, and corrosions and damages of the coil board 11 can be preferably prevented. The coil board 11 is functioned as a means of magnetic field generation or a means of magnetic field detection. For example, it is materialized by piling multi-layer coil portion 12 on glass epoxy board or the like. The coil board is supposed to refer to the above publication as described in detail, and an explanation thereof will not be further described.

A pin 102 is constituted to provide a ball-like protrusion on a base like a form of thin disc to form a part of plastics 101. The pin 102 is a means for securing a silicone rubber band 111 (plastic band, or band made of silicone), 121 (plastic band), as described later, to the sensor 1. The detail thereof will be later described.

The nail contact portion 103 is a portion being in contact with a finger nail when the sensor 1 is attached to the finger of subject for experiment in a part of the plastics 101 to have a curve directed along a form of the finger. The subject for experiment can have a comfortable feeling of wearing when the sensor 1 is attached to the finger by the nail contact portion 103 having this curve. As the nail contact portion 103 is made of relatively soft plastics, the subject for experiment can have a comfortable feeling of wearing and reduce a possibility damaging nail or skin.

Figure 2D:
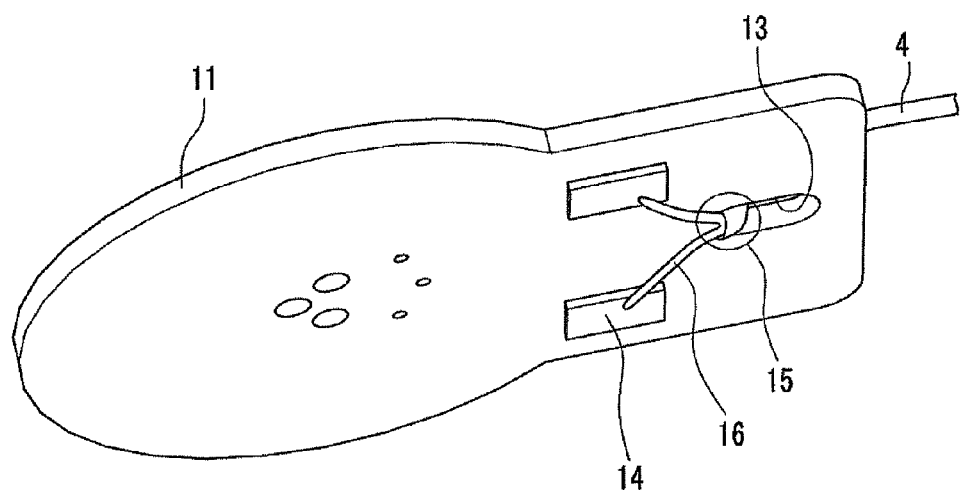
FIG. 2D is a view showing a reverse side of a coil board.

FIG. 2D is a view showing a reverse side of the coil board 11. In a reverse side of the coil board 11, a conducting wire 16 of the coil portion 12 is adhered by soldering at a solder joint portion 14. The conducting wire 16 is connected to the cable 4. The cable 4 is let off from a reverse side of the coil board 11 through a hole 13 to a front side of the coil board 11. A connection between the conducting wire 16 and the cable 4 is adhered by an adhesion portion 15 to the coil board 11.

Figure 3A:
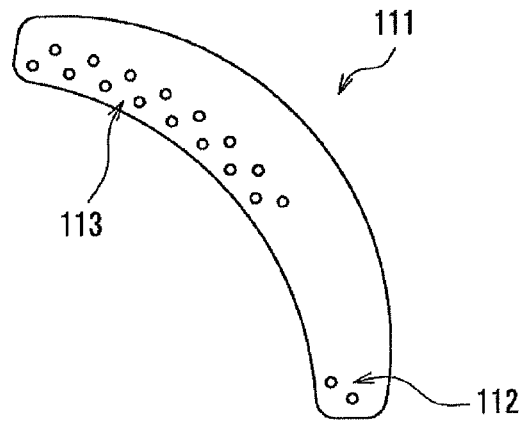
FIG. 3A is a view seeing an outer appearance of a silicone rubber band of this embodiment.

In such a way, a tensile strength of the conducting wire 16 is remarkably increased by letting out the cable 4 from a reverse side of the coil board 11 through the hole 13 to the surface side and adhering the connection between the conducting wire 16 and the cable 4 to the coil board 11 at the adhesion portion 15. In case that the cable 4 is pulled, a whole force thereof does not travel directly, and the conducting wire or the like can be prevented from cutting itself. The load applied to the solder joint portion 14 can be remarkably decreased and a fitting of the conducting wire 16 can be confirmed for sure. As shown in FIG. 3A, a silicone rubber band 111 as one example of the plastic band is thin in thickness, and the whole body is formed like a substantially crescent swelling in the middle seeing from top (in case of a direction perpendicular to the thickness). The silicone rubber band 111 has two holes 112 and sixteen holes 113.

Figure 3B:
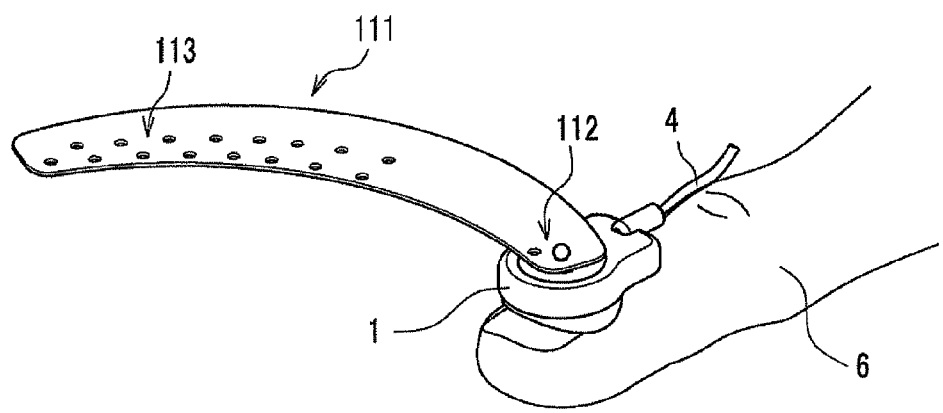
FIG. 3B is a view showing an appearance just before the sensor is attached to a finger with the silicone rubber band.
Figure 3C:
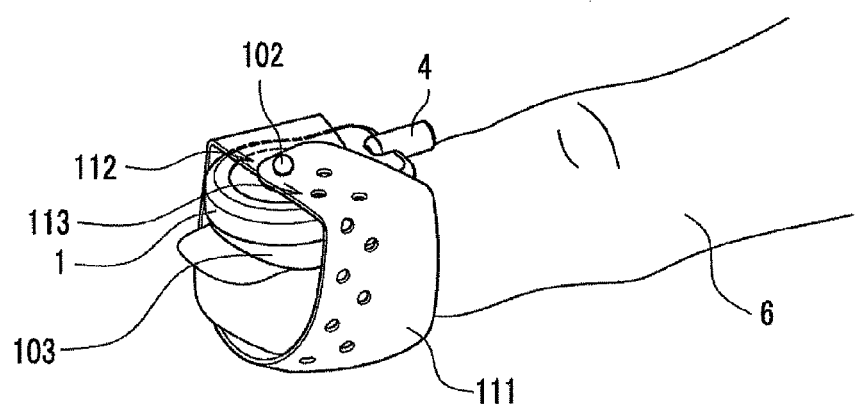
FIG. 3C is a view showing an appearance as the sensor attached to the finger with the silicone rubber band.

As shown in FIG. 3B, when the sensor 1 is attached to a finger 6, the pin 102 is designed to pass through one of holes 112 of the silicone rubber band 111 of the sensor 1, and a swelling side of the silicone rubber band 111 is set to be placed in the base side. Thereafter, as shown in FIG. 3C, the silicone rubber band 111 is wound around the finger 6 to pass the pin 102 in one of the holes 113 in a slightly tensile condition. Then, in case where the sensor 1 is attached to the finger 6, the silicone rubber band 111 can be uniformly in contact with the whole finger 6 and a stable feeling of wearing can be obtained.

Figure 4:
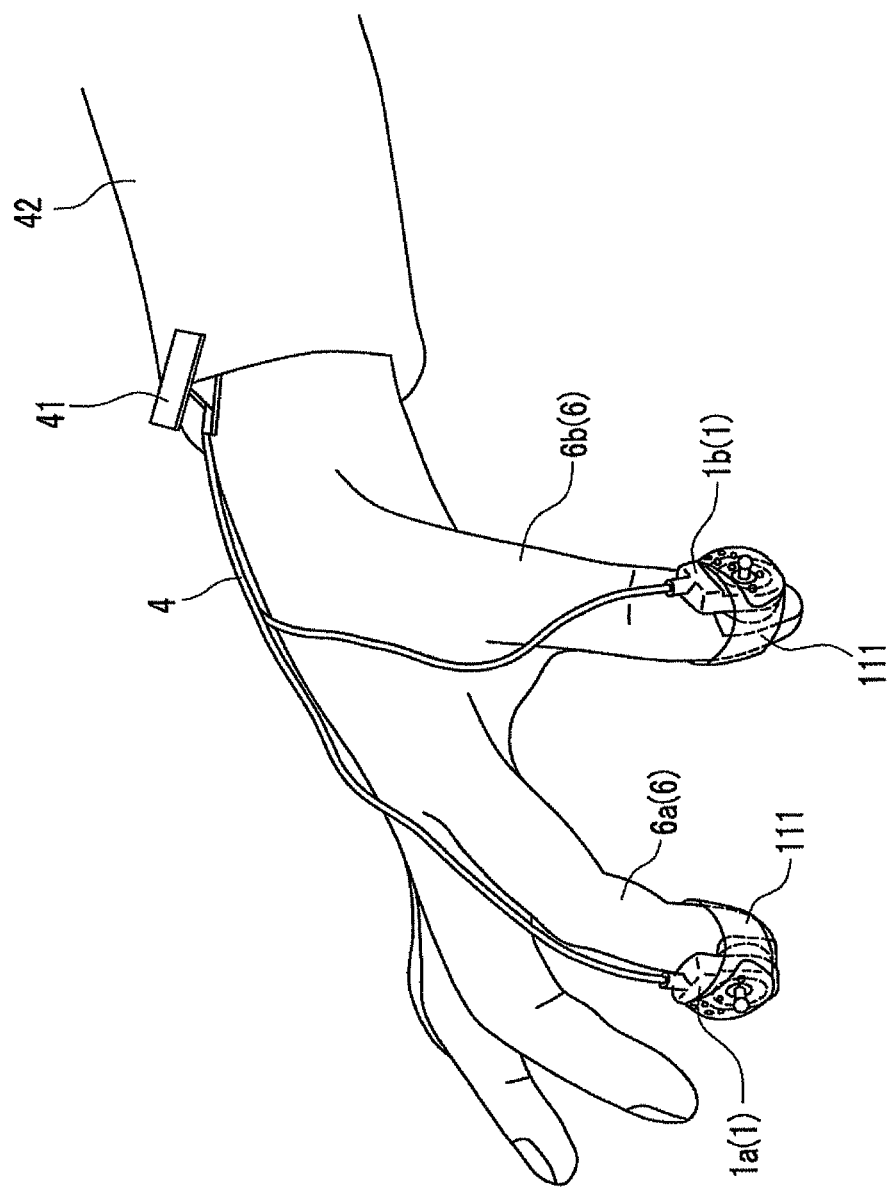
FIG. 4 is a view showing an appearance as the sensors attached respectively to a thumb and a forefinger.

As shown in FIG. 4, the sensor 1a can be attached by the silicone rubber band 111 to a finger (forefinger) 6a and the sensor 1b can be attached by the silicone rubber band 111 to a finger (thumb) 6b. In this case, when the cable 4 is adhered by a cable clip 41 to clothes 42, an accident, as the sensor pulled by the cable 4, can be effectively avoided, then the stability for attaching the sensor 1 to the finger 6 can be remarkably improved. The subject for experiment makes the finger-tapping movement in a condition shown in FIG. 4.

Figure 5A:
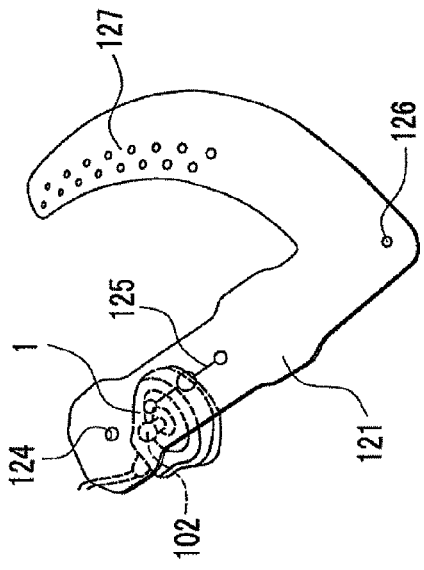
FIG. 5A is a view showing an outer appearance of the other example of the silicone rubber band.

Next, the other example of the silicone rubber band will be described. As shown in FIG. 5A, a silicone rubber band 121 comprises a sensor cover 122 wound around the sensor 1 and a finger holder 123 having a substantially crescent form (a part thereof and the sensor cover 122 are mutually overlapped, a portion substantially forming a crescent) wound around the finger 6. The sensor cover 122 and the finger holder 123 are integrally constituted to be substantially like a letter "L".

The sensor cover 122 is provided with a hole 124, a slit 125, and a hole 126. The finger holder 123 is provided with sixteen holes 127 besides the hole 126.

Next, the steps to attach the sensor 1 to the finger 6 with the silicone rubber band 121 will be described.

Figure 5B:
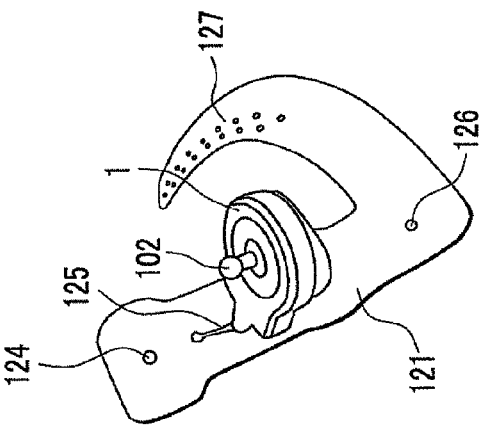
FIGS. 5B to 5D are views respectively showing appearances as the silicone rubber bands attached to fingers in a time series.
Figure 5C:
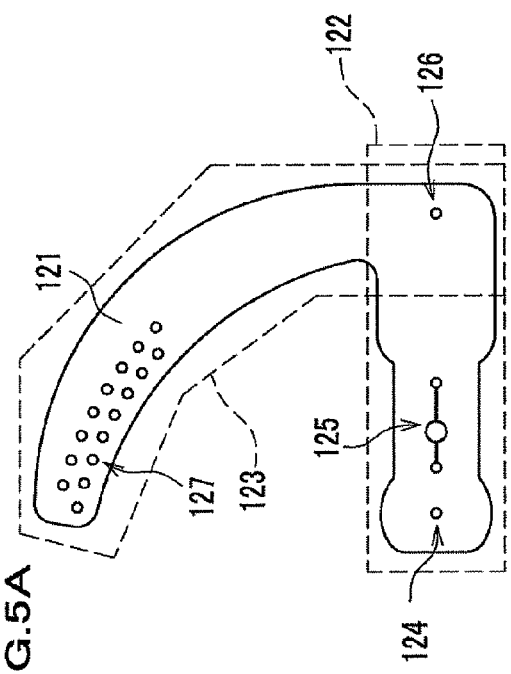
Figure 5D:
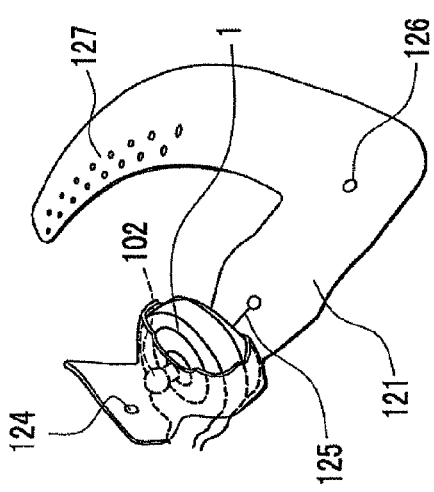

At first, as sequentially shown in FIG. 5B to 5D, the sensor 1 is passed through the slit 125 of the silicone rubber band 121.

Figure 6B:
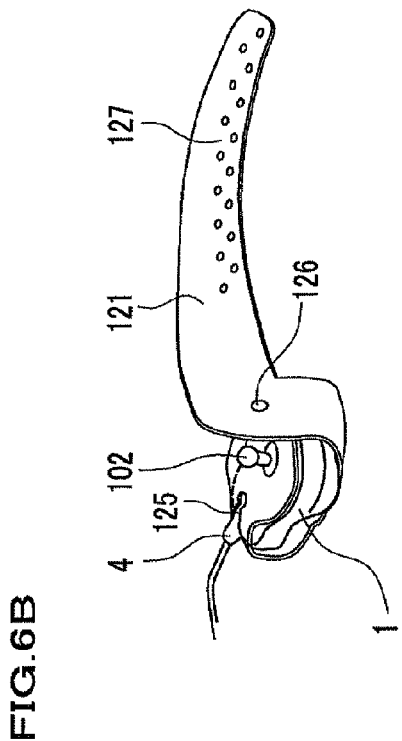
FIG. 6A to 6D are views showing appearances as the silicone rubber bands in the other example attached to fingers in a time series in sequence of FIG. 5D.
Figure 6D:
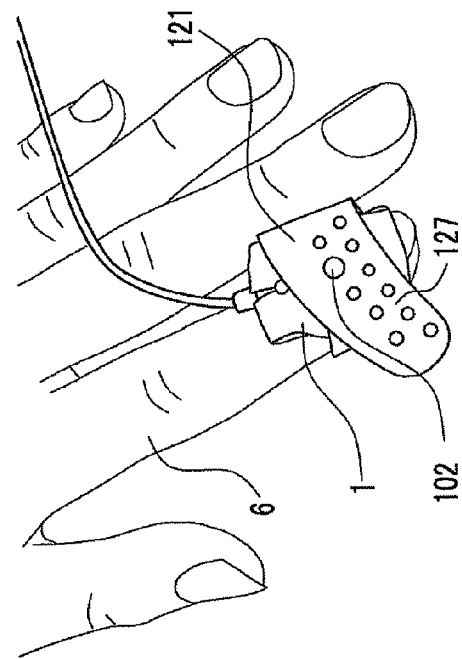
Figure 6A:
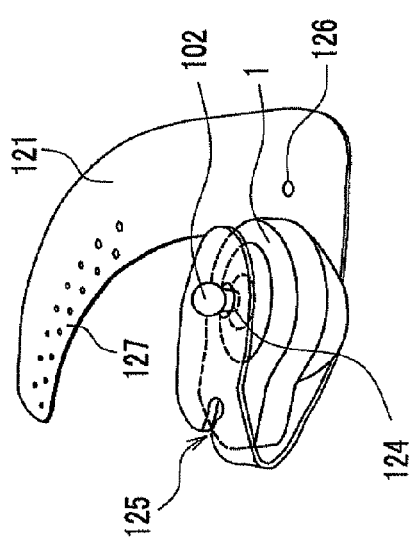
Figure 6C:
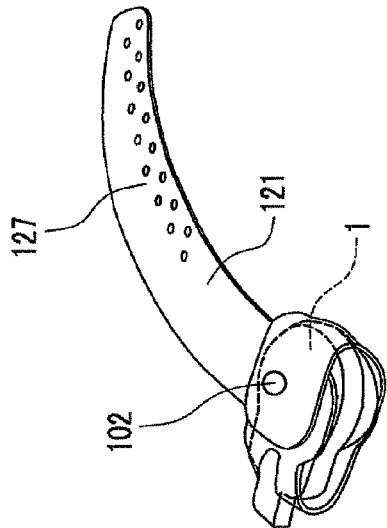

Next, as shown in FIG. 6A, the pin 102 of the sensor 1 is passed through the hole 124 of the silicone rubber band 121. Next, as shown in FIGS. 6B and 6C in sequence, the pin 102 of the sensor 1 is passed through the hole 126 of the silicone rubber band 121. Then, as shown in FIG. 6D, the silicone rubber band 121 is wound around the finger 6 to pass the pin 102 through one of the holes 127 in a slightly tensile condition.

In such a way, when the sensor 1 is attached to be wound around the finger 6 with the silicone rubber band 121, as the finger holder 123 of the silicone rubber band 121 is in a uniform contact with the whole finger 6 by that the finger holder 123 of the silicone rubber band 121 forms like a substantially crescent, a stable feeling of wearing can be obtained as well as the case of the silicone rubber band 111.

As the silicone rubber band 121 is integrally constituted by the sensor cover 122 and the finger holder 123, it makes no possibility for attaching to the finger 6 with the finger holder 123 turned upside down in a swelling direction of substantially crescent form thereof.

When the silicone rubber band 121 is attached to the finger 6 with the finger holder 123 turned upside down in a swelling direction of substantially crescent form thereof, the finger holder 123 is not in uniform contact with whole finger 6. Then, as a feeling of discomfort as a part of the finger 6 pressed occurs, a subject for experiment can notice or understand a mistaken way of wearing.

As the sensor 1 is covered by the sensor cover 122, the sensor 1 is not in direct contact with the finger 6. Accordingly, in case where the sensor 1 is made of materials possible to cause an allergic reaction, a possibility for causing an allergic reaction can be greatly decreased for a subject for experiment. It is mild or gentle to be in contact with the finger 6, as it is made of silicone to be softer than the plastics 101 of the sensor 1. Furthermore, the friction caused by being in contact with the finger 6 becomes large and it can be effectively prevented from occurring a slide between the sensor 1 and the finger 6 (nail).

In case of breaking the silicone rubber band 121 or in case of cleaning or washing, the silicone rubber band 121 and the sensor 1 can be easily separated.

The slit 125 is provided in a position and a magnitude as shown in FIG. 5A. When the silicone rubber band 121 is wound around the sensor 1, the both can be mutually in close contact, and the stability for attaching the sensor 1 to the finger 6 can be improved.

Figure 7A:
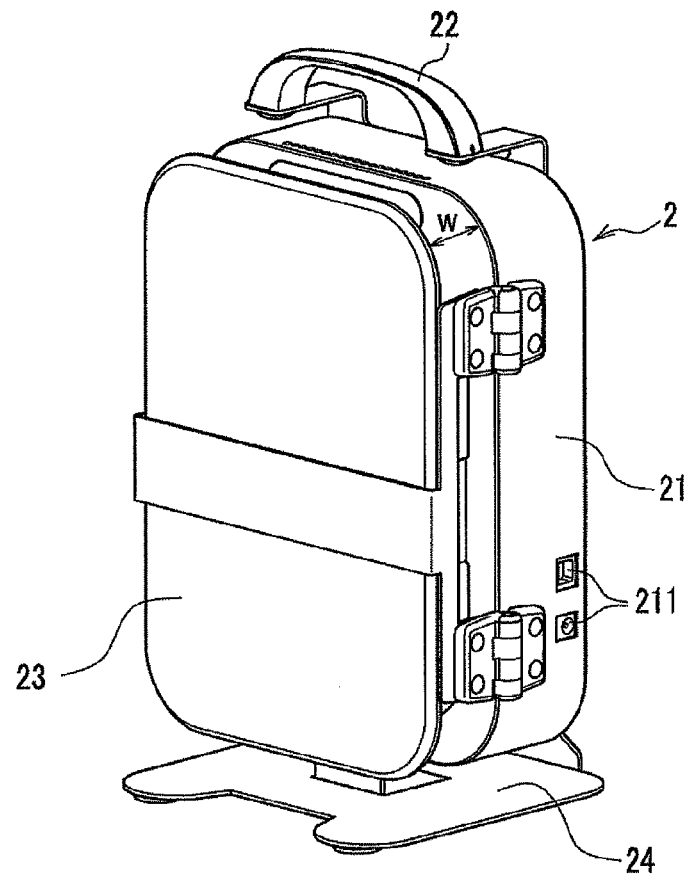
FIG. 7A is a view showing an appearance of the device for measuring motor function relating to this embodiment.
Figure 7B:
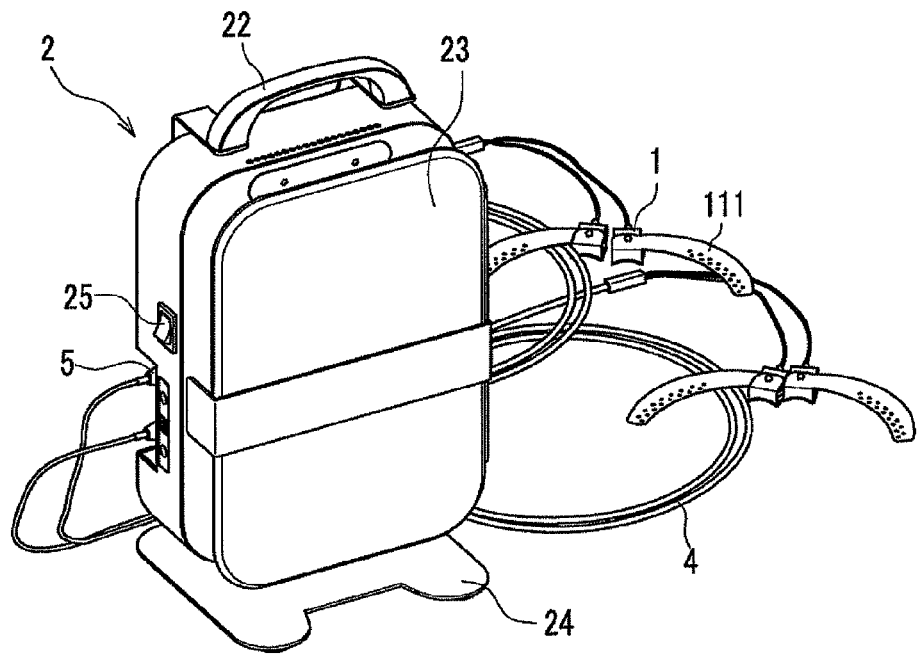
FIG. 7B is a view showing an appearance as the sensor connected through the cable and the connector to the device for measuring motor function.

Next, a constitution of the device for measuring motor function 2 will be described. As shown in FIGS. 7A and 7B, the device for measuring motor function 2 is constituted by a main body portion 21, a grip 22, a panel 23 (door), and a base 24.

The main body portion 21 is formed like a substantially parallelepiped shape to house an AC generator 201 (Referring to FIG. 1), a current detector 202 (Referring to FIG. 1), and an A/D converter 203 (Referring to FIG. 1) therein. The main body portion 21 is provided with an Input/Output terminal 211 used for connecting to the analyzer 3 with cables, and power source switch 25 for switching On-or-Off of the device for measuring motor function 2.

The grip 22 is attached to the main body portion 21 and is positioned to be upper in a vertical direction of center of gravity of the device for measuring motor function 2 when it is supported by the base 24. As the grip 22 is provided in such a position, the device for measuring motor function 2 does not tilt at the time of lifting the device for measuring motor function 2 with the grip 22 held. Then, it is convenient for transporting or the like. As a space under the grip 22 as shown in Figures can be maintained to be large, a person carrying the device for measuring motor function 2 is easy to hold the grip 22.

The panel 23 is openably or closably attached by a hinge to the main body portion 21. The width w formed between the panel 23 and the main body portion 21 is constituted not to pinch user's finger in this gap, that is, to be around 20 mm in this description.

The base 24 is designed to be a member supporting the main body portion 21 and has a space for containing the main body portion 21 and the panel 23 seeing from top (in case of a direction seeing from the grip 22).

Figure 8A:
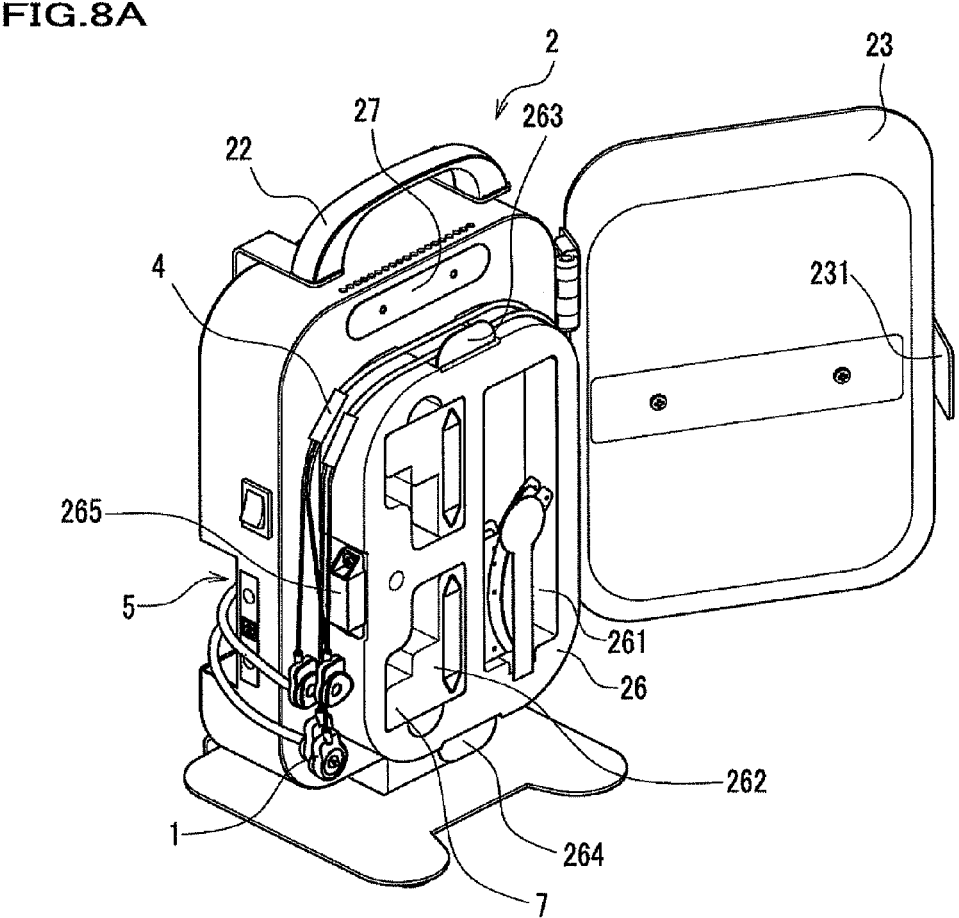
FIG. 8A is a view showing the device for measuring motor function with its panel being open of the present invention.

As shown in FIG. 8A, the main body portion 21 is provided with a storage section 26 and a lamp 27 at a portion to be seen at the time of opening the panel 23.

The storage section 26 is used for winding the cable 4 connected to the sensor 1 in an outer circumference. For example, it is made of sponge member. The storage section 26 is provided with a storage section of replacement silicone rubber band 261, storage section of calibration block 262, hooks 263, 264, and a magnet for holding panel 265.

The storage section of replacement silicone rubber band 261 is a space for housing the silicone rubber band 111, 121. Then, the silicone rubber band 111, 121 may be housed in a bag.

The storage section of calibration block 262 is a space for housing the calibration block 7. The calibration block 7 is an equipment used for calibration in relationship between the voltage data and the distance between fingers. As each of subjects for experiment has a difference in magnitude of fingers or the like, the subject for experiment grasps the calibration block 7 with his or her thumb and forefinger and calibrates by understanding a relationship between voltage data and distance between fingers. In addition, the calibration using the calibration block 7 will be referred to the above publication as described in detail, and a further explanation thereof will be omitted.

The hooks 263, 264 are members for preventing the cable 4 wound around an outer circumference of the storage section 26 from protruding outside.

Accordingly, various problems such as a case where the panel 23 cannot be closed by an intervention between the storage section 26, as the cable 4 wound around an outer circumference of the storage section 26 and protruded outside, and the panel 23, when the panel 23 is closed, or a case where the cable 4, as protruded as the above, damages, can be effectively prevented before anything happens.

The magnet for holding the panel 265 is designed to magnetically attract a metal portion 231 provided in the panel 23. Then, the panel 23 as closed is attached to the main body portion 21 in stability. The magnet for holding the panel 265 also plays a role to prevent the cable 4 wound around an outer circumference of the storage section 26 from protruding outside as well as the hooks 263, 264.

As above mentioned, according to the device for measuring motor function 2, the sensor 1 not in use and the cable 4 can be housed in compact by winding them around the storage section 26, it is easy to carry the device for measuring motor function 2, and the sensor 1 and the cable 4 can be protected from the outside situation.

As the storage section 26 is constituted by the sponge member, the possibility for damaging the cable wound around the storage section 26 or the sensor 1 can be decreased.

As the storage section of replacement silicone rubber band 261 housing the silicone rubber bands 111, 121 and the storage section of calibration block 262 housing the calibration block 7 are provided inside the storage section 26 for winding the sensor 1 and the cable 4, the space thereof can be effectively used.

Figure 8B:
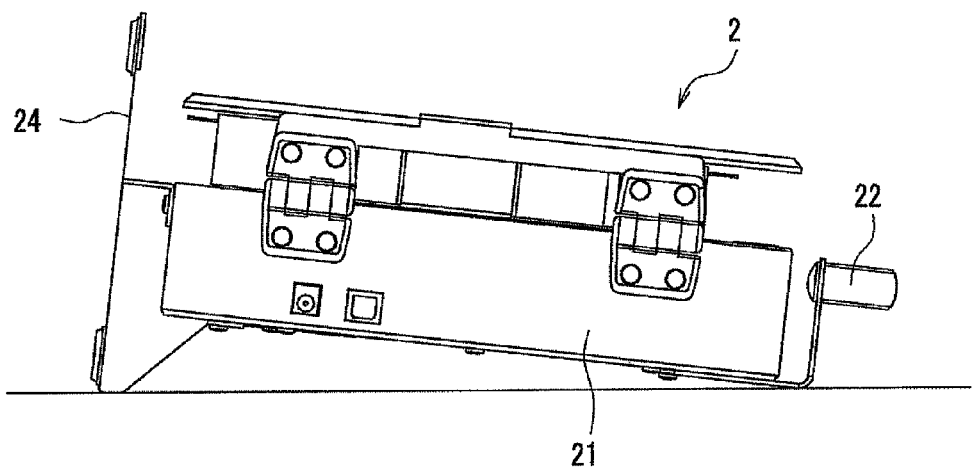
FIG. 8B is a view showing an appearance as the device for measuring motor function disposed in a lateral direction.

The base 24 is large enough to contain the main body portion 21 and the panel 23 as seen from top. Then, as shown in FIG. 8B, the device for measuring motor function 2 is constituted to unnaturally have an oblique angle, when the device for measuring motor function 2 is placed in a lateral direction. Thus, as the user comes to feel a sense of discomfort at the time of opening or closing the panel 23, and winding the cable 4 around the storage section 26, or the like, it makes a user to promote a use as placed in a longitudinal direction of the device for measuring motor function 2.

As an embodiment of the present invention has been described, the present invention is not limited to the above, but can be done within a range not to change gist or essence thereof. For example, a finger for attaching the sensor 1 is not limited to a thumb or a forefinger, but may be the other finger such as a middle finger.

The material of plastic band may not be made of silicone, but material other than silicone can be used if it is more excellent or substantially the same in quality of the property such as elasticity, softness, strength, durability, waterproof, biological safety, and temperature characteristics (the elasticity or the like is inconstant in case of varying in temperature). In a specific constitution, it may be appropriately changed without departing from a gist of the present invention.

What is claimed is:

1. A sensor for measuring motor function, comprising:
 a magnetic field generator configured to be attached to a first human finger and to generate a magnetic field by electrification supplied from outside, the magnetic field generator having a first plastic body, a first coil board covered with the first plastic body, and a first pin which is integrally provided on the first plastic body;
 a magnetic field detector configured to be attached to a second human finger and to output electric current corresponding to a change of distance between the magnetic field generator and the magnetic field detector by relative motion therebetween and to a strength of the magnetic field generated in the magnetic field generator, the magnetic field detector having a second plastic body, a second coil board covered with the second plastic body, and a second pin which is integrally provided on the second plastic body; and
 a plastic band configured to be attached to one of the first and second human fingers while covering the magnetic field generator or the magnetic field detector associated with the one of the first and second human fingers;
 wherein the plastic band has a plurality of through holes and is configured to be detachably attached to one of the first and second pins by passing the first pin of the magnetic field generator or the second pin of the magnetic field detector associated therewith through a first through hole of the plurality of through holes, winding the plastic band around the finger, and passing the first pin or second pin through a second through hole of the plurality of through holes while covering the magnetic field generator or the magnetic field detector associated with the one of the first and second human fingers,
 wherein the plastic band overlaps itself with the second through hole overlapping the first through hole with the first pin or second pin passed through the first through hole and second through hole when the plastic band is wound around the finger,
 wherein the plurality of through holes comprises a first through hole row consisting of through holes arranged in a direction in which the plastic band can be wound around the first or second human finger and a second through hole row consisting of other through holes arranged in the same direction as the through holes of the first through hole row, wherein the second through hole is in one of the first through hole row or second through hole row,
 wherein the first and second through hole rows are arranged side by side, in a direction of an axis of the first or second human finger,
 wherein there is only one pin arranged as the first pin in the magnetic field and as the second pin in the magnetic field detector respectively, and
 wherein each of the first and second pins can pass through any hole of any of the first through hole row and the second through hole row when each of the first and second pins passes through the first through hole and second through hole while the plastic band is wound around the finger.

2. The sensor for measuring motor function according to claim 1,
 wherein the magnetic field generator and the magnetic field detector are configured to form a curve directed along an external shape of the first and second human fingers, respectively.

3. The sensor for measuring motor function according to claim 1,
 wherein each of the first and second coil boards has a through hole for passing a cable for electrically connecting to the coil board.

4. The sensor for measuring motor function according to claim 1,
 wherein the plastic band comprises silicone.

5. The sensor for measuring motor function according to claim 1,
 wherein the sensor includes a nail support contact portion having a curved surface to be in contact with a finger nail.

6. The sensor for measuring motor function according to claim 1,
 wherein first and second through hole rows are arranged so that the plurality of through holes are in zigzag alignment.

7. The sensor for measuring motor function according to claim 1,
 wherein a whole shape of the plastic band is crescent-shaped.

8. The sensor according to claim 1,
wherein the plastic band comprises a crescent-shaped portion configured to be wound around the one of the first and second human fingers, and a rectangular sensor cover configured to be wound around the magnetic field generator or the magnetic field detector,
wherein the crescent-shaped portion and the sensor cover are integrally formed in a shape of a letter "L",
wherein the first through hole is in a portion of the plastic band that is common to the crescent-shaped portion and sensor cover,
wherein the plurality of through holes includes a third through hole in the sensor cover,
wherein the plastic band is further configured to be detachably attached to one of the first and second pins by passing the first pin of the magnetic field generator or the second pin of the magnetic field detector associated therewith through the first, second, and third through holes of the plurality of through holes while covering the magnetic field generator or the magnetic field detector associated with the one of the first and second human fingers, and
wherein the plastic band overlaps itself with the first through hole overlapping the third through hole when the plastic band is wound around the finger.

9. The sensor for measuring motor function according to claim 1, wherein the first through hole is in one of the first through hole row or second through hole row.

10. A device for measuring motor function electrically connected through a cable and a connector to a magnetic field generator and a magnetic field detector in a sensor for measuring motor function as claimed in claim 1, comprising:
an AC generator configured to generate an alternating current supplied to the magnetic field generator and a current detector to detect an electric current generated by the magnetic field detector; and
a main body portion housing the AC generator and the current detector, and a door configured to be openably or closably attached to the main body portion,
wherein the main body portion comprises a storage section housing the cable connected to the magnetic field generator and the magnetic field detector to wind the cable therearound.

11. The device for measuring motor function according to claim 10,
wherein the storage section comprises a sponge member.

12. The device for measuring motor function according to claim 10,
wherein the storage section is provided with at least two hooks for preventing the cable from protruding to a side of the door.

13. The device for measuring motor function according to claim 10,
wherein the main body portion is formed to be rectangular, and the device for measuring motor function comprises a base designed to support the main body portion and to contain the main body portion and the door.

14. The device for measuring motor function according to claim 13,
wherein the device for measuring motor function is provided with a grip attached to the main body portion and positioned above a center of gravity thereof at the time of supporting by the base.

15. The device for measuring motor function according to claim 10,
wherein the plastic band comprises silicone.

* * * * *